(12) United States Patent
Lu et al.

(10) Patent No.: US 10,869,610 B2
(45) Date of Patent: Dec. 22, 2020

(54) SYSTEM AND METHOD FOR IDENTIFYING CARDIAC ARRHYTHMIAS WITH DEEP NEURAL NETWORKS

(71) Applicant: General Electric Company, Schenectady, NY (US)

(72) Inventors: Weijia Lu, Shanghai (CN); Joel Xue, Wauwatosa, WI (US); Shuyan Gu, Shanghai (CN); Jie Shuai, Shanghai (CN); Lifei Hu, Beijing (CN)

(73) Assignee: General Electric Company, Schenectady, NY (US)

(*) Notice: Subject to any disclaimer, the term of this patent is extended or adjusted under 35 U.S.C. 154(b) by 57 days.

(21) Appl. No.: 16/210,688

(22) Filed: Dec. 5, 2018

(65) Prior Publication Data

US 2020/0178825 A1 Jun. 11, 2020

(51) Int. Cl.
| | | |
|---|---|---|
| *A61B 5/024* | (2006.01) | |
| *A61B 5/046* | (2006.01) | |
| *A61B 5/00* | (2006.01) | |
| *G06N 3/08* | (2006.01) | |
| *A61B 5/0464* | (2006.01) | |
| *A61B 5/0245* | (2006.01) | |
| *A61B 5/0468* | (2006.01) | |
| *A61B 5/04* | (2006.01) | |

(52) U.S. Cl.
CPC ............ *A61B 5/046* (2013.01); *A61B 5/0245* (2013.01); *A61B 5/02405* (2013.01); *A61B 5/0464* (2013.01); *A61B 5/7264* (2013.01); *A61B 5/7275* (2013.01); *G06N 3/08* (2013.01); *A61B 5/0006* (2013.01); *A61B 5/04012* (2013.01); *A61B 5/0468* (2013.01); *A61B 5/7257* (2013.01)

(58) Field of Classification Search
CPC ... A61B 5/046; A61B 5/02405; A61B 5/0245; A61B 5/0464; A61B 5/7264; A61B 5/7275; A61B 5/0006; A61B 5/04012; A61B 5/0468; A61B 5/7257; G06N 3/08
See application file for complete search history.

(56) References Cited

U.S. PATENT DOCUMENTS

| | | | | |
|---|---|---|---|---|
| 2002/0143576 A1* | 10/2002 | Nolvak | ................. | A61B 5/0002 705/2 |
| 2018/0140203 A1* | 5/2018 | Wang | .................... | A61B 5/0205 |
| 2019/0059763 A1* | 2/2019 | Shakur | ................. | A61B 5/0456 |
| 2019/0328243 A1* | 10/2019 | Nemati | ................. | A61B 5/7253 |
| 2019/0332900 A1* | 10/2019 | Sjolund | ................. | A61N 5/1039 |
| 2020/0037961 A1* | 2/2020 | Smital | ................... | A61B 5/7221 |

* cited by examiner

*Primary Examiner* — Ankit D Tejani
*Assistant Examiner* — Joshua Brendon Solomon
(74) *Attorney, Agent, or Firm* — Andrus Intellectual Property Law, LLP

(57) ABSTRACT

A system for identifying arrhythmias based on cardiac waveforms includes a storage system storing a trained deep neural network system, wherein the trained deep neural system includes a trained representation neural network and a trained classifier neural network. A processing system is communicatively connected to the storage system and configured to receive cardiac waveform data for a patient, identify a time segment in the cardiac waveform data, and transform the time segment into a spectrum image. The processing system is further configured to generate, with the representation neural network, a latent representation from the spectrum image, and then to generate, with the classifier neural network, an arrhythmia classifier from the latent representation.

20 Claims, 8 Drawing Sheets

SYSTEM AND METHOD FOR IDENTIFYING CARDIAC ARRHYTHMIAS WITH DEEP NEURAL NETWORKS

BACKGROUND

The present disclosure generally relates to cardiac monitoring, such as electrocardiography, and more particularly, to automatic detection of cardiac abnormalities from cardiac waveforms with deep neural networks.

An arrhythmia is an abnormal heart rhythm. Before treatment, it is important for a doctor to know where an arrhythmia starts in the heart and the characteristics of the arrhythmia. An electrocardiogram (ECG) is often used to diagnose arrhythmias. Systems and methods for interpreting electrocardiograph (ECG) waveforms are currently available to assist a clinician in interpreting waveforms and assessing patient cardiac health based on ECG waveforms. Currently available systems and methods generally process ECG waveform data and provide suggested interpretations based thereon. These currently available systems and methods generally require processing ECG waveforms to identify certain predefined waveform features, and those identified features provide the basis for arrhythmia detection. For example, many interpretation systems utilize proprietary feature extraction algorithms.

BRIEF DESCRIPTION

This Brief Description is provided to introduce a selection of concepts that are further described below in the Detailed Description. This Brief Description is not intended to identify key or essential features of the claimed subject matter, nor is it intended to be used as an aid in limiting the scope of the claimed subject matter.

One embodiment of a system for identifying arrhythmias based on cardiac waveforms includes a storage system storing a trained deep neural network system, wherein the trained deep neural system includes a trained representation neural network and a trained classifier neural network. A processing system is communicatively connected to the storage system and configured to receive cardiac waveform data for a patient, identify a time segment in the cardiac waveform data, and transform the time segment into a spectrum image. The processing system is further configured to generate, with the representation neural network, a latent representation from the spectrum image, and then to generate, with the classifier neural network, an arrhythmia classifier from the latent representation.

One embodiment of a method for identifying arrhythmias based on cardiac waveforms includes identifying a time segment of cardiac waveform data for a patient and transforming the time segment into a spectrum image. A representation neural network generates a latent representation from the spectrum image. An arrhythmia classifier is then generated from the latent representation by a classifier neural network.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Current systems and methods for interpreting ECG waveforms require feature extraction, and thus development of feature extraction algorithms has been a focus of arrhythmia detection for many years. Through their extensive experimentation and research in the relevant field, the inventors have recognized that such feature extraction algorithms can be limiting and create inaccuracies for arrhythmia detection systems. Moreover, the inventors have recognized that limiting pre-processing of ECG waveforms for arrhythmia detection is also desirable. Accordingly, the inventors have developed a novel deep neural network system and training structure that requires minimal pre-processing of ECG waveforms and does not require feature extraction or waveform parameter identification prior to providing the ECG data to the neural network system.

The disclosed deep neural network system includes an image processing neural network trained to process cardiac waveform data in order automatically identify and annotate arrhythmias therein. Only minimal pre-processing is required to transform the raw cardiac waveform data into a spectrum image, which is an image representing the spectral content of a time segment of cardiac waveform data. For example, the spectrum image is a two-dimensional image, with transient frequency distribution of the ECG waveform on one axis and time on the second axis. The value at each grid point or pixel in the image represents the amplitude of the respective spectral presence within the cardiac waveform data at the given point and time. For example, the spectrum image may be a grayscale representation of the 2-D spectrum as exemplified in FIGS. 3B and 4B, where high amplitude represented as white and zero amplitude as black.

The spectrum image is provided as input to the trained deep neural network system, which then generates an arrhythmia classifier from the image input. The arrhythmia classifier characterizes the presence or absence of a predetermined list of rhythm types for which the deep neural network system is trained to identify. For example, the deep neural network system may be trained to identify various arrhythmias, including asystole, supraventricular tachycardia, ventricular fibrillation, ventricular tachycardia, atrial fibrillation, normal sinus rhythm, or any subset of those rhythms or other known arrhythmia types. For example, the deep neural network system may output an arrhythmia classifier comprising a classification value indicating the presence or absence of each rhythm type in the pre-determined list of rhythm types for which the deep neural network system is trained.

Figure 1A:
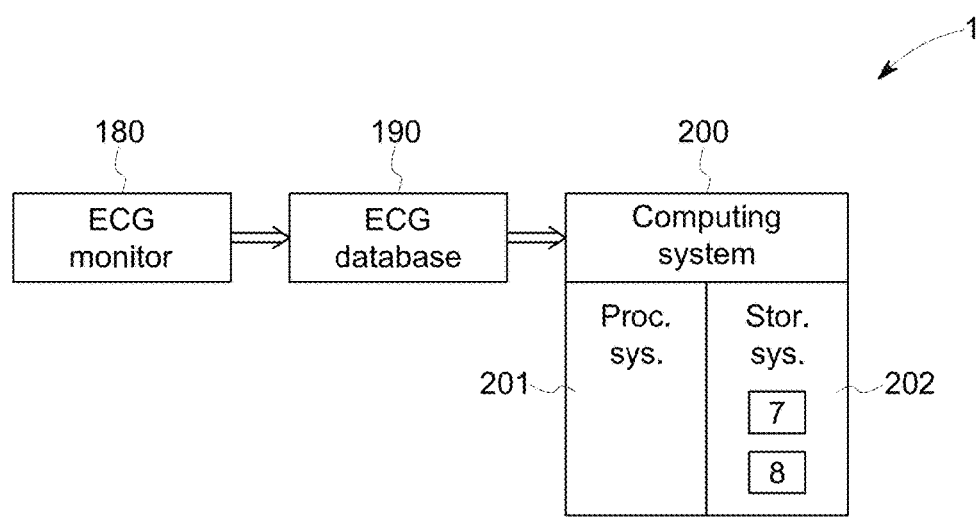
FIG. 1A is a block diagram of a system for identifying arrhythmias based on cardiac waveforms including a deep neural network system.
Figure 1B:
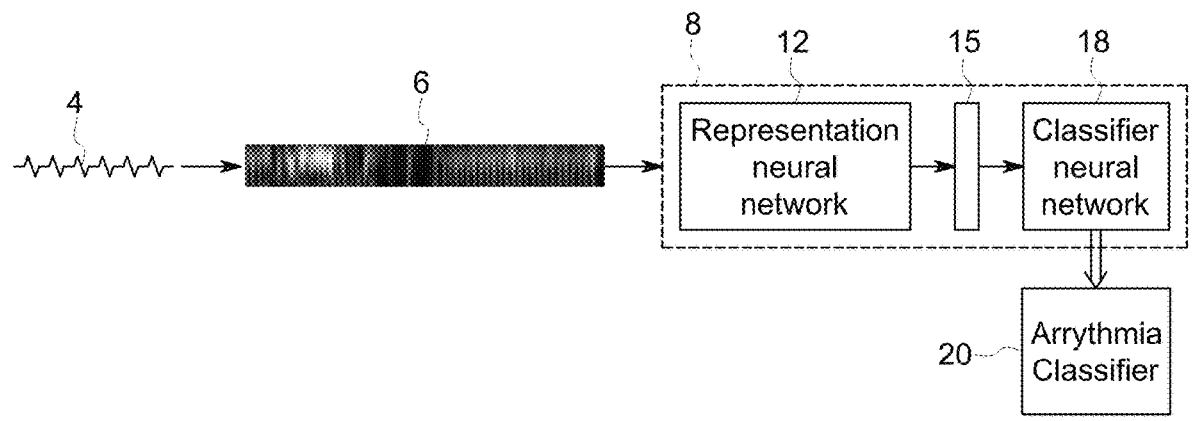
FIG. 1B is a flow diagram of a deep neural network system and method for arrhythmia identification.

FIGS. 1A and 1B are high-level schematic depictions of an exemplary system and method for identifying arrhythmias utilizing a trained deep neural network system. FIG. 1A depicts one embodiment of a system for identifying arrhythmias comprising a deep neural network architecture 8 and a pre-processing module 7, which comprise software housed within a computing system 200. In the pre-processing module 7, cardiac waveform data for a patient is divided into time segments 4, such as one lead of ECG data divided into sequential time segments of a pre-defined length. The time segment 4 of cardiac wave data is transformed into a spectrum image 6, such as via Fast Fourier transform (FFT), or more specifically, a Short Time window Fast Fourier transform (SFFT).

The image is then provided to a trained deep neural network system 8 that includes a trained representation neural network 12 that generates a latent representation 15 from the spectrum image 6 and a trained classifier neural network 18 that generates an arrhythmia classifier 20 from the latent representation. The representation neural network 12 functions to generalize the frequency spectrum present in the spectrum image 6. This can be loosely analogized to principal component identification, where the trained representation neural network 12 identifies the principal frequency components depicted in the spectrum image, eliminates redundant information and reduces the number of pixels represented. Thus, the latent representation 15 generated by the representation neural network 12 may be smaller in one or both dimensions than the spectrum image 6 provided as input.

The latent representation 15 is then fed to the classifier neural network 18 which is trained to predict the presence or absence of the arrhythmia types of interest. For example, the classifier neural network 18 may exhibit temporal dynamic behavior for a time sequence, such as a recurrent neural network (RNN) which allows sequential time-domain processing of the time segments 4 of the cardiac waveform data. The RNN takes current segment and previous segment information into consideration when performing classifications, versus a convolutional neural network (CNN) which only takes current segment information when performing classification. The classifier neural network 18 outputs the arrhythmia classifier 20. For example, the arrhythmia classifier may be a list of values classifying the presence or absence of each of several rhythm types, such as for a predetermined list of rhythm types that the deep neural network system 8 has been trained to detect.

Referring to FIG. 1A, cardiac waveforms are recorded by an ECG monitor 180, and the cardiac waveforms for the patient are stored in an ECG database 190. The ECG database 190 may be, for example, a dedicated cardiac database, such as comprising part of a MUSE ECG management system by General Electric Company. Alternatively, the ECG database 190 may be a patient's medical record, or other storage location and structure for the ECG waveform. In other embodiments, the cardiac waveform data may be provided directly from the ECG monitor 180 to the computing system 200 housing the system 1 for arrhythmia detection in accordance with embodiments described herein.

The computing system 200 may be any of various types of known computing systems, including an edge device or a cloud computing system. In one embodiment, the computing system 200 is an edge computer server. In another embodiment, the computing system 200 is a virtual private cloud (VPC). The computing system 200 generally comprises a processing system 201 and a storage system 202. The processing system 201 is communicatively connected to the storage system 202 in order to load and execute software from the storage system 202, including the pre-processing module 7 and the deep neural network system 8. The pre-processing module 7, comprises computer-readable instructions that are executable by the processing system 201 to identify and filter the time segment 4 of cardiac waveform data and the spectrum image 6, such as in accordance with embodiments described herein. The storage system 202 also stores the trained deep neural network system 8 which is employed by the processing system 201 to output the arrhythmia classifier 20 in accordance with embodiments described herein. The processing system includes one or more processors. The storage system comprises any of various types of storage media. Examples of storage media include random access memory, read-only memory, optical disks, flash memory, virtual memory, non-virtual memory, a magneto-optical disk, CD-ROM, or a nonvolatile memory card.

Figure 2:
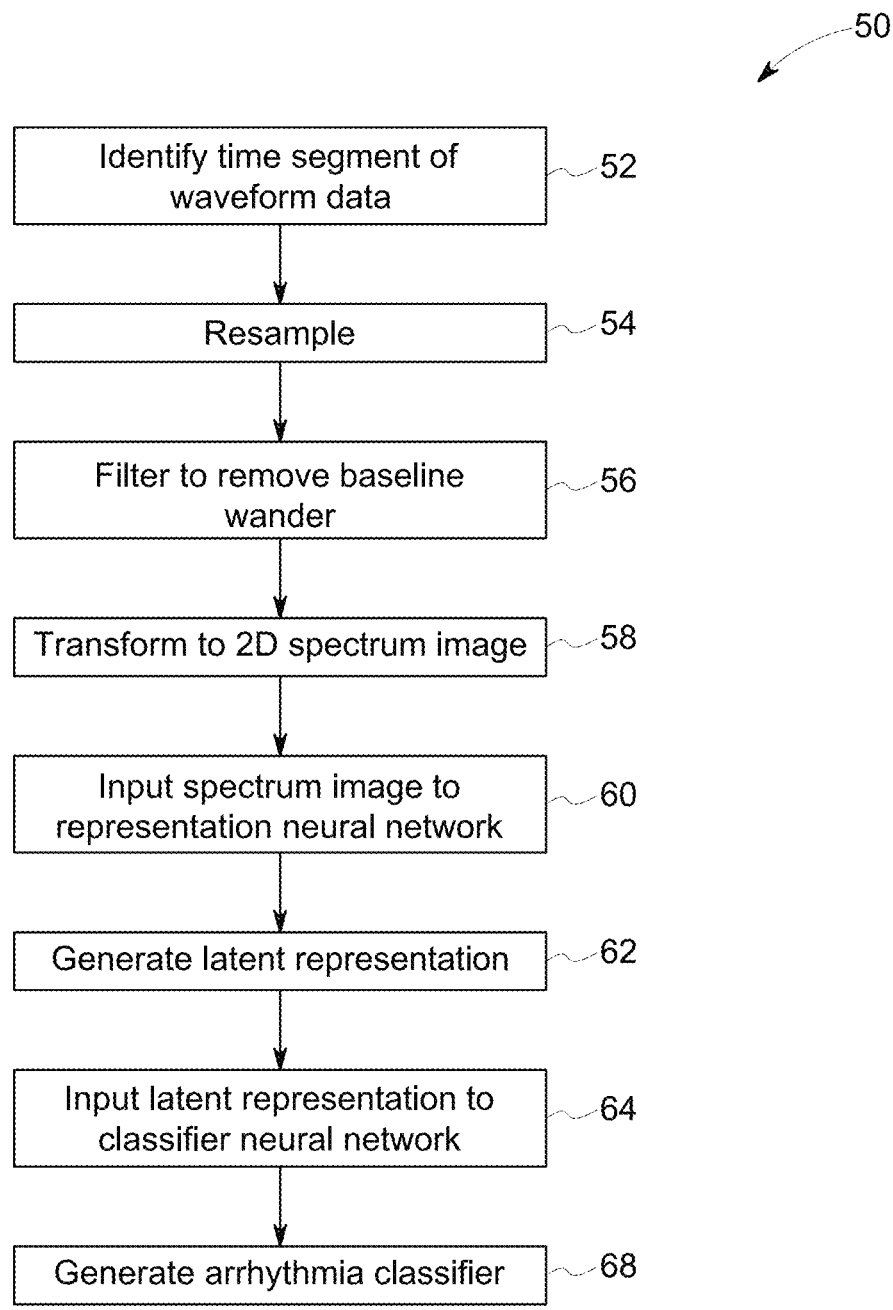
FIG. 2 is a flow diagram providing high-level illustration of a method for automatically identifying arrhythmias based on cardiac waveforms using a deep neural network system according to an exemplary embodiment.

FIG. 2 is a flowchart describing at a high level one exemplary method for identifying arrhythmias. A time segment of cardiac waveform data is identified at step 52. The length of the time segment 4 may be defined based on the pre-determined list of rhythm types being detected. Each rhythm type has a definition which can be related to a minimum length of time required for detection. For example, asystole is defined as no heart rate for at least four seconds. Thus, the minimum length of time required to detect asystole is four seconds. As another example, sinus bradycardia is defined as a heart rate of less 40 bpm for at least 5 heartbeats. Thus, the minimum length of time required to detect sinus bradycardia is at least 7.5 seconds. As yet another example, sinus tachycardia is defined as a heart rate greater than 140 bpm for at least 17 beats. Thus, the minimum length of time to ensure sufficient data for sinus tachycardia detection is about 7.3 seconds. Various other arrhythmias may be considered, and the length of the time segment 4 is defined to accommodate the longest minimum time duration needed to detect all types of arrhythmias in the pre-determined list of rhythm types. In one embodiment where asystole, supraventricular tachycardia, ventricular flutter or fibrillation, and ventricular tachycardia are interrogated, the length of the time segment of cardiac waveform data is 13 seconds. In other embodiments, the length of the time segment may be shorter or longer to accommodate various system constraints and considerations.

The time segment is then pre-processed—e.g., utilizing the pre-processing module 7—in order to generate the spectrum image 6 to be provided to the trained deep neural network system 8. For instance, once a time segment of waveform data is identified at step 52, such as a 13-second sample, and the data is resampled at step 54 so as to reformat the data to a consistent sample frequency. To provide just one example, the raw ECG data may be from a cardiograph and sampled at 500 kHz or may be from a Holter monitor and sampled at 120 kHz, and all such data may be resampled at 200 kHz in order to normalize all inputs to provide a consistent sample frequency into the network system 8. The re-sampled data is then filtered at step 56 to remove baseline wander. For example, a high-passed FIR filter may be employed. The filtered data is then transformed to a spectrum image at step 58. For example, the two-dimensional spectrum image may be computed based on Welch's method, such as 1024 points of fast Fourier transform operated on a 91% overlapped moving window with a span of 60 samples. The spectrum image 6 is then provided as input to the trained deep neural network at step 60, and specifically to the representation neural network portion thereof. A latent representation is generated by the representation neural network 12 at step 62. The latent representation 15 is then provided as input to the classifier neural network 18 at step 64. The classifier neural network then generates the arrhythmia classifier at step 68.

Figure 3:
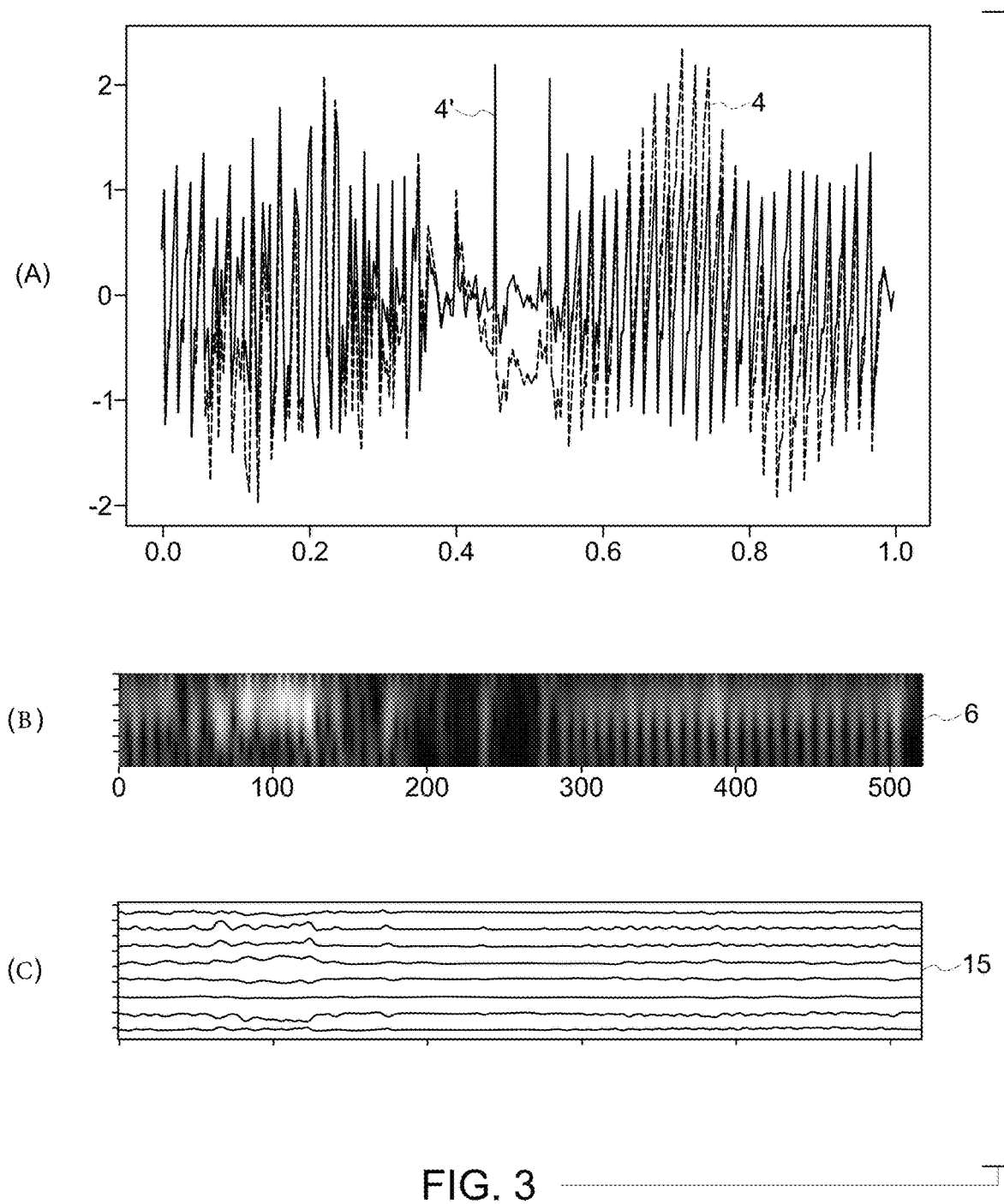
FIG. 3 depicts an exemplary time segment of cardiac waveform data, a corresponding spectrum image generated therefrom, and a latent representation.
Figure 4:
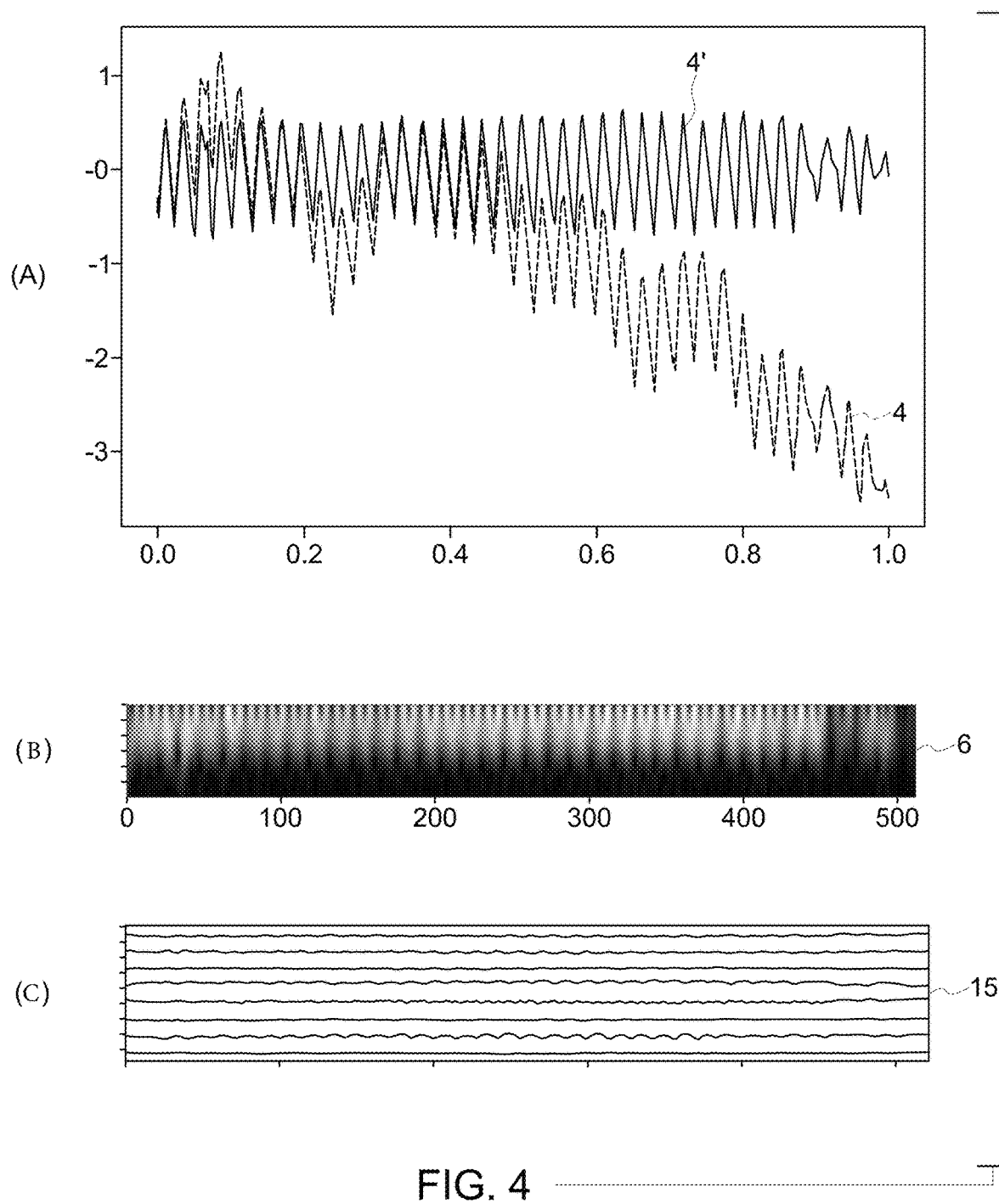
FIG. 4 depicts another embodiment of a time segment of cardiac waveform data, a corresponding spectrum image generated therefrom, and a latent representation.

FIGS. 3 and 4 provide exemplary depictions of time segment 4 data and the resulting spectrum images 6. FIG. 3 exemplifies a waveform exhibiting ventricular tachycardia, whereas FIG. 4 depicts a waveform exhibiting a waveform exhibiting sinus tachycardia. In each of FIGS. 3A and 4A, the raw time segment 4 of cardiac data is shown, along with the filtered time segment 4' which has been filtered to remove baseline wander and re-sampled. FIGS. 3B and 4B depict the spectrum image 6 for each filtered time segment 4'. FIGS. 3C and 4C are a graphical representation of a latent representation 15 of the filtered time segment 4' of cardiac data, thus graphically depicting an output of the representation neural network 12 when the respectively filtered time segment 4' is provided as input. In the depicted examples, the amplitude of each line gives the mean and its width gives the standard deviation of Gaussian distribution. In the depicted embodiment, the dimension of latent space is equal to 8. In other embodiments, the dimension may be greater than or less than 8.

Figure 5:
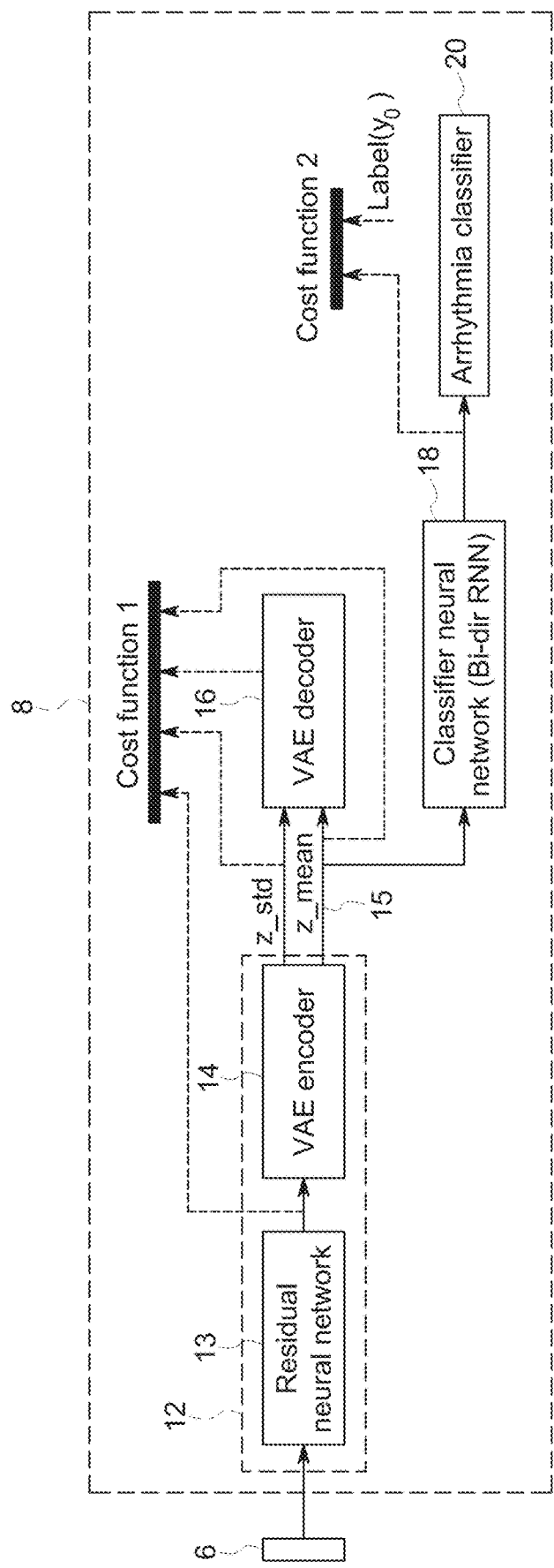
FIG. 5 is a schematic diagram illustrating an exemplary deep neural network system including training structures.

FIG. 5 depicts an exemplary neural network structure of a deep neural network system 8, including neural network structures used in the training of the representation neural network 12 in the classifier neural network 18. In the depicted example, the deep neural network system 8 comprises the representation neural network 12 and the classifier neural network 18 in an end-to-end arrangement where the neural networks are distinct with no overlap and are trained separately and sequentially. FIG. 5 also depicts aspects of the training structure for the representation neural network 12 and the classifier neural network 18. The representation neural network 12 is trained by unsupervised learning, and is trained first. The trained representation neural network 12 then provides initialization for training the classifier neural network 18, which may be trained by supervised learning. For example, the classifier neural network 18 may include a bi-directional RNN structure with an attention window, along with multiple dense layers. The span of the attention window increases from the bottom layer to the top layer. Therefore, the learning starts with the details and proceeds to the overall picture. The bi-directional RNN reuses the output from previous time segments in order to generate the arrhythmia prediction for each input with sequential information.

In the depicted embodiment, the representation neural network 12 comprises a variational auto-encoder (VAE). The VAE encoder 14 comprises part of the representation neural network 12 and generates the latent representation 15. Specifically, the VAE encoder generates a vector of means (z_mean) and a vector of standard deviations (z_std). The mean vector is utilized as the latent representation 15 inputted into the classifier neural network 18. While VAEs traditionally serve to provide generative modeling, here it is used to generate a robust latent representation and to decrease the noise in each sample. The VAE encoder 14 constrains the distribution of each latent cluster and learns the distribution. This is in contrast to a deterministic representation provided by prior art systems which seek to initially define and extract a set of predefined features from the cardiac waveform. As shown by the comparative test results described herein below, use of the VAE in this way proves to be an effective first step in producing successful arrhythmia identification.

The VAE decoder 16 is used to train the VAE encoder 14, but is not employed in the final trained deep neural network system 8. The representation neural network 12 also comprises a residual neural network 13 to perform feature extraction. For example, the residual neural network 13 may be a convolutional neural network (CNN). The representation neural network 12 may also include one or more additional convolutional layers, such as a pooling layer (see FIG. 6).

In the depicted embodiment, the output of the residual neural network 13 trained for feature extraction and the output of the VAE decoder 16 are provided as inputs to the first cost function for training the representation neural network 12. The representation neural network 12, and in particular the VAE encoder 14, are trained to minimize the mean error, as well as to minimize the standard deviation error. For example, the VAE encoder 14 of the representation neural network 12 may be trained by the following cost function:

$$\text{loss}_1 = E_{z \sim q_\theta(x|x_i)}[|x_i - p_\phi(\tilde{x}_i)|^2 | z] + KL(q_\theta(z|x_i) \| p(z|x))$$

The cost function is a reconstruction loss based on the input to the VAE encoder, which is denoted by $q_\theta(z|x_i)$, compared to the output of the decoder, which is denoted by $p_\phi(\tilde{x}_i|z)$. The first term in the above listed loss equation (referred to herein as the first loss equation) is normally referred to as reconstruction loss. This term encourages the decoder to learn to reconstruct the data. If the decoder(s) output does not reconstruct the data well, it will incur a large cost in this loss function. The second term in the first loss function is the Kullback-Leibler divergence between the encoders distribution $q_0$ and $p(z|x)$. This divergence measures how much information is lost when using to q represent p, and it acts as a regularlizer penalty to maintain latent distribution into sufficiently diverse clusters. This Kullback-Leibler term is often referred to as latent loss.

The representation neural network 12 is trained until a certain threshold cost is met. At that point, the representation neural network 12 is fixed and then the classifier neural network 18 is trained by supervised training. The classifier neural network 18 may be trained, for example, by utilizing a cross entropy loss function as provided in the following loss equation (herein referred to as the second loss equation):

$$\text{loss}_2 = -E\left(\sum_{y=1}^{M} I_{y=y_o} \log(P_{y|x_o})\right)$$

where y and $y_o$ is the predicted and true label, respectively, M is the total number of rhythm type categories, I(•) is indicator function and $P_{y|x_o}$ is predicted distribution.

Figure 6:
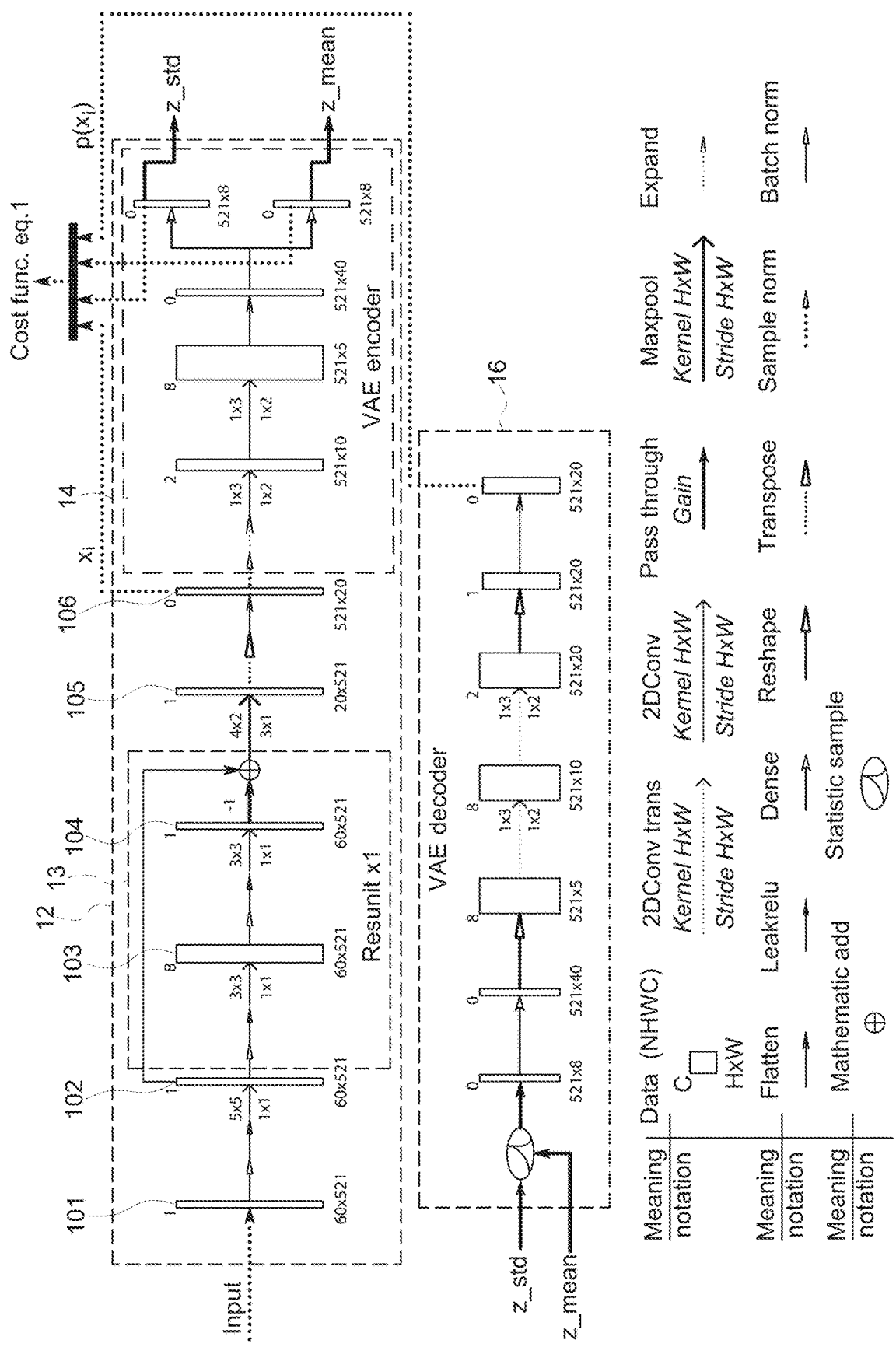
FIG. 6 provides a more detailed schematic diagram illustrating exemplary layers of a representation neural network and also illustrating exemplary training structures and methods therefor.

FIG. 6 shows an exemplary layer structure and training method for the representation neural network 12, and FIG.

7 depicts an exemplary layer structure and training for the classifier neural network 18. For example, a training data set may comprise databases of ECG records that are annotated and marked where rhythm changes occur and labeled with the arrhythmia type exhibited therein (i.e., one of the predetermined list of rhythm types). For example, the training dataset may be processed such that the time segments (e.g. a thirteen-second segment) are identified around the annotation, such as selected from a limb lead. The time segments are then resampled, filtered, and transferred to spectrum images as described above.

In this example, the highest dimension of each data block represents the size of the batch (N) which is hidden in this diagram. The other three dimensions are height (H), width (W), and feature channels (C). For instance, the first block shows a data batch with shape equal to N (e.g., 140)×60×521×1. Each inputted sample is a 2-D spectrum image with one gray channel, 60 frequency bins, and 521 sampling points. Furthermore, each figure shows the network configuration, including the kernel and stride size of filtering (marked on both sides of the operator arrow), the number of residual units (equals 1), and the dimension of latent representation (equals 8).

The representation neural network 12 comprises several convolutional layers providing input to the VAE encoder 14. In the depicted example, the representation neural network 12 includes a first convolutional layer 101, a second convolutional layer 102, a third convolutional layer 103, a fourth convolutional layer 104, a fifth convolution layer 105, and a sixth convolutional layer 106, leading up to the VAE encoder 14 comprising three additional layers. The various layer types are described according to the notation at the bottom of the figure. For example, the first convolutional layer 101 through the fourth convolutional layer 104 are each kernel-type convolution filters. The training strategy for each of the layer outputs is indicated by the arrows, the meaning of which is noted at the bottom of FIG. 6. For example, the first layer 101, which is a kernel-type convolutional filter, has applied batch normalization and an activation function of leaky relu. The second and third layers are the same. A shortcut is provided from the second layer to the mathematic add following the fourth layer 104, which forms the residual neural network 13. Additional convolutional layers, including pooling layer 105, are included prior to the VAE encoder 14 portion.

The residual neural network 13 generates the feature vector (20 floats) from the frequency vector (60 frequency bins). The output vectors of the VAE encoder 14 are 521 samples long with only 8 floats. Thus, the representation neural network 12 in the depicted embodiment, compresses the sample from 60 frequency bins in the input image to 8 floats in the output vector.

The VAE is trained according to the first cost function. The input to the cost function is illustrated in FIG. 6, which as described above includes the reconstruction loss term and the Kullback-Liebler divergence (latent loss) term. From these two loss terms, a fraction η can be calculated to represent the portion of latent loss in the total loss of each iteration. This fraction can be coupled into the model training processing to dominate the Gaussian distribution, from which the encoder output is sampled. In the beginning, the reconstruction loss comprises a larger portion of the total loss. Therefore, the fraction is small and latent variable z is drawn from normal distribution N (z_mean, η z_std) during sampling instead of N (z_mean, z_std). By this manner, the large standard deviation in the beginning is partially bypassed and the convergence speed of the training is increased.

As described above, the VAE encoder 14 outputs a mean vector and a standard deviation vector (z_mean, z_std). Both vectors are provided as input to the VAE decoder which are each statistically sampled to create a sampled latent vector which is processed by the various layers of the VAE decoder 16. The output of the VAE decoder 16 is provided, on a batch basis, to the first cost function.

Figure 7:
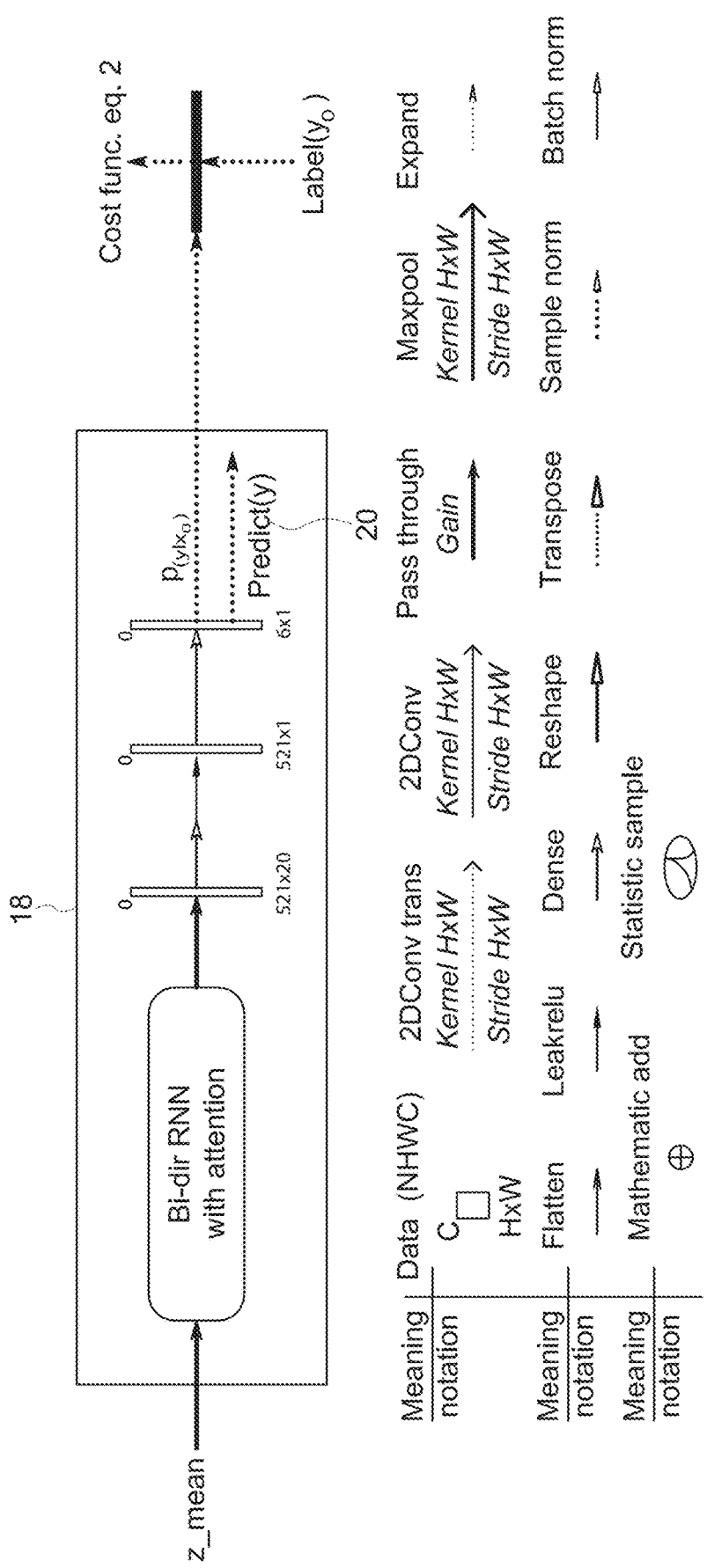
FIG. 7 provides a more detailed schematic diagram illustrating exemplary layers of a classifier neural network and also illustrating exemplary training structures and methods therefor.

Once the representation neural network 12 is trained, that network is frozen and its output is provided as input to train the classifier neural network. The mean vector output from the VAE encoder 14 is utilized as the latent representation 15 input into the classifier neural network 18. For example, the bi-directional RNN is trained by a cross entropy loss function depicted in the second cost function provided above. The inputs to the above-described cost function are depicted in FIG. 7. In the embodiment shown, and also described above, the classifier neural network 18 is a bi-directional RNN. In FIG. 7, it should be noted that for the bi-directional RNN with attention, the hidden unit size in the RNN cell equals ten, the number of layers in the bi-directional RNN network is four, and the smallest attention window size lump on the RNN output is three.

The disclosed system and method were trained and tested in a five-fold cross-validation study. The trained deep neural network architecture 8 was encapsulated into a docker image and deployed to either an edge computer server or a virtual private cloud (VPC). During the initialization of the docker container in the edge server, the local working directory was mounted and the data was fed into the trained deep neural network system 8 by a local file I/O. Tables II and III below give the performance rates on test sets using the structure depicted in FIGS. 6 and 7, which were trained on ECG records representing normal sinus rhythms (sinus), asystole (asys), sinus tachycardia (tachy), ventricular flutter or fibrillation (VF/VFL), and ventricular tachycardia (VT). The following tables give the performance rates on test data sets from the MIT arrhythmia database (labeled #0 VFDB and #1 VFDB):

TABLE II

CONFUSION MATRIX ON #0
VFDB TEST SET IN 5 FOLD CV DESIGN
(ACCURACY = 90%)

| Type | Asys | Tachy | VF/VFL | VT |
|---|---|---|---|---|
| # PP/Tot | 48/52 | 19/20 | 398/444 | 335/372 |
| Sensitivity | 0.92 | 0.95 | 0.89 | 0.9 |
| Precision | 0.74 | 0.70 | 0.96 | 0.9 |

TABLE III

CONFUSION MATRIX ON #1
VFDB TEST SET IN 5 FOLD CV DESIGN
(ACCURACY = 90%)

| Type | Asys | Tachy | VF/VFL | VT |
|---|---|---|---|---|
| # PP/Tot | 46/52 | 16/20 | 399/444 | 345/372 |
| Sensitivity | 0.88 | 0.80 | 0.89 | 0.93 |
| Precision | 0.82 | 0.72 | 0.94 | 0.89 |

From these tables it is proven that the proposed network has promising sensitivity in the detection of these arrhythmias. Moreover, the test results show good precision rates in each of the arrhythmias. Accordingly, this method has proven to significantly improve the accuracy of arrhythmia detection, as well as the speed of convergence.

Figure 8:
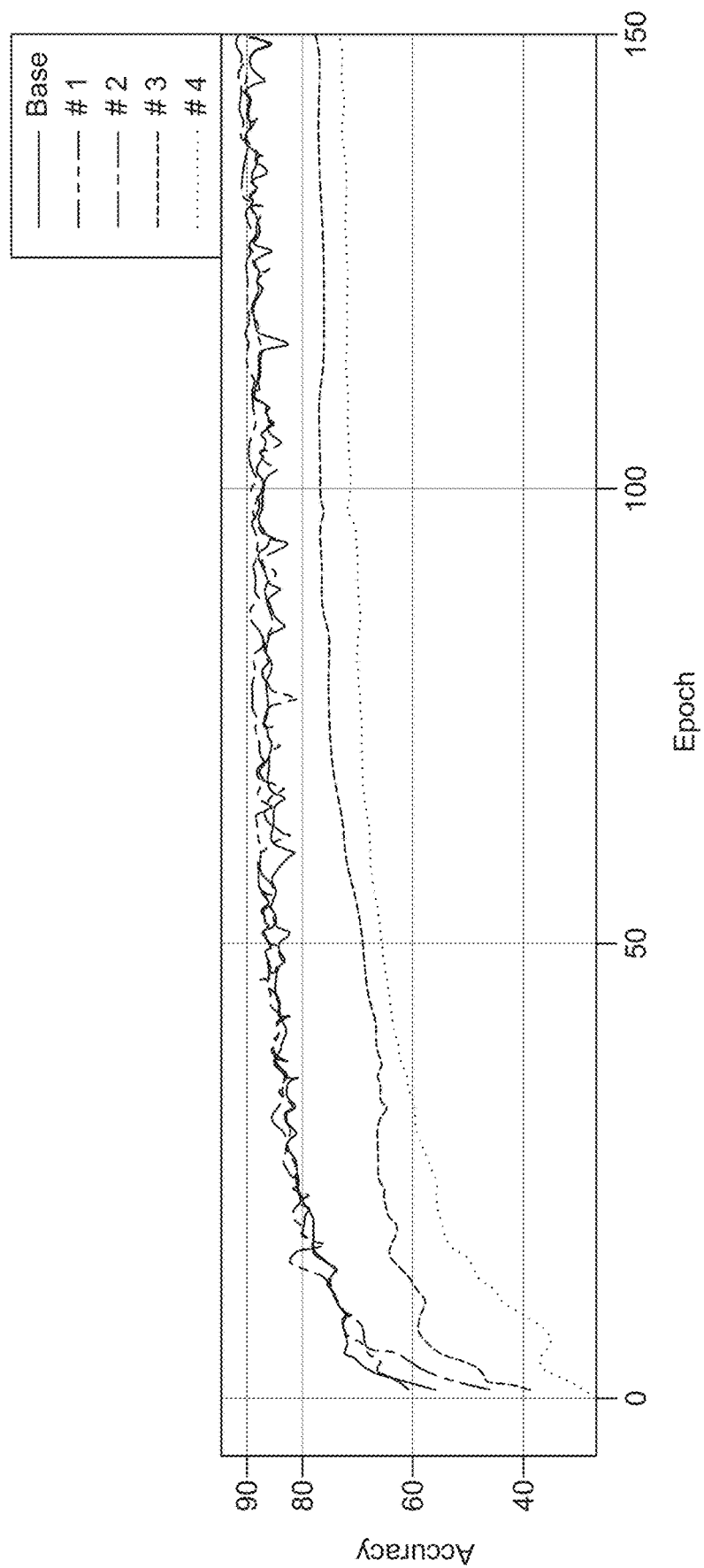
FIG. 8 is a graph depicting validation study results testing the disclosed deep neural network system.

Finally, a comparative experiment was conducted, the results of which are depicted in FIG. 8. Set up parameters of the deep neural network were varied for each test: 1) the number of hidden units in the RNN cell was varied from 10 to 15; 2) the size of the smallest attention window was changed from 3 to 5 and the number of layers from 4 to 3; 3) the VAE and the adjusted network from test #1 (changing the hidden unit size) was replaced with a dense projection; 4) the VAE and the test #2 configuration (changing the attention window) was replaced with a dense projection. As is illustrated in FIG. 8, it is proven that the latent distribution learned by the VAE significantly boosts the speed of convergence and accuracy. Meanwhile, the other configuration changes in the setup (#1 and #2) did not make a significant difference in the model performance.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A system for identifying arrhythmias based on cardiac waveforms, the system comprising:
a storage system storing a trained deep neural network system, wherein the trained deep neural network system includes a trained representation neural network and a trained classifier neural network;
a processing system communicatively connected to the storage system and configured to:
receive cardiac waveform data for a patient;
identify a time segment of the cardiac waveform data;
transform the time segment of the cardiac waveform data into a spectrum image;
generate, with the representation neural network, a latent representation from the spectrum image; and
generate, with the classifier neural network, an arrhythmia classifier from the latent representation.

2. The system of claim 1, wherein the arrhythmia classifier includes a classifier value for each of a predetermined list of rhythm types.

3. The system of claim 2, wherein the predetermined list of rhythm types includes at least two of a normal sinus rhythm, asystole, supraventricular tachycardia, ventricular fibrillation, ventricular tachycardia, and atrial fibrillation.

4. The system of claim 3, wherein the representation neural network includes a variational autoencoder (VAE) encoder neural network, wherein the VAE encoder neural network outputs the latent representation.

5. The system of claim 4, wherein the neural network system includes the trained representation neural network and the trained classifier neural network organized sequentially such that the latent representation output of the VAE encoder is fed directly to the classifier neural network to generate the arrhythmia classifier.

6. The system of claim 4, wherein the representation neural network further includes a convolutional neural network.

7. The system of claim 1, wherein the classifier neural network comprises a bidirectional recurrent neural network (RNN).

8. The system of claim 1, wherein the representation neural network and the classifier neural network are sequentially arranged and sequentially trained neural networks with no overlap.

9. The system of claim 1, wherein the spectrum image is a two-dimensional image representing transient frequency distribution on one axis and time on a second axis.

10. The system of claim 1, wherein the time segment is identified in a limb lead of a multi-lead ECG.

11. A method for identifying arrhythmias based on cardiac waveforms, the method comprising:
identifying a time segment of a cardiac waveform data for a patient;
transforming the time segment of cardiac waveform data into a spectrum image;
generating, by a trained representation neural network, a latent representation from the spectrum image; and
generating, by a trained classifier neural network, an arrhythmia classifier from the latent representation.

12. The method of claim 11, wherein the arrhythmia classifier includes a classifier value for each of a predetermined list of rhythm types, including two or more of a normal sinus rhythm, asystole, supraventricular tachycardia, ventricular fibrillation, ventricular tachycardia, and atrial fibrillation.

13. The method of claim 11, wherein the representation neural network further comprises a variational autoencoder (VAE) encoder neural network, wherein the VAE encoder neural network outputs the latent representation used by the classifier neural network to generate the arrhythmia classifier.

14. The method of claim 13, further comprising training the representation neural network to minimize mean error and to minimize standard deviation error.

15. The method of claim 11, wherein the classifier neural network comprises a bidirectional recurrent neural network (RNN), and further comprising training the classifier neural network using a cross entropy loss function.

16. The method of claim 11, wherein the representation neural network and the classifier neural network are sequentially arranged and trained neural networks with no overlap.

17. The method of claim 11, wherein the spectrum image is a two-dimensional image representing transient frequency distribution on one axis and time on a second axis.

18. The method of claim 11, wherein the time segment is identified in a limb lead of a multi-lead ECG.

19. The method of claim 18, wherein a length of the time segment is defined based on a predetermined list of rhythm types that the classifier neural network is trained to identify.

20. The method of claim 11, further comprising pre-processing the time segment of cardiac waveform data to remove baseline wander normalize sample rate.

* * * * *